United States Patent
Cunningham et al.

(10) Patent No.: US 9,604,892 B2
(45) Date of Patent: Mar. 28, 2017

(54) PLASMA ARC FURNACE WITH SUPERCRITICAL $CO_2$ HEAT RECOVERY

(76) Inventors: Stephen L. Cunningham, Altadena, CA (US); Martin A. Stuart, Burbank, CA (US)

( * ) Notice: Subject to any disclaimer, the term of this patent is extended or adjusted under 35 U.S.C. 154(b) by 38 days.

(21) Appl. No.: 14/234,460

(22) PCT Filed: Aug. 3, 2012

(86) PCT No.: PCT/US2012/049508
§ 371 (c)(1),
(2), (4) Date: Jan. 23, 2014

(87) PCT Pub. No.: WO2013/020042
PCT Pub. Date: Feb. 7, 2013

(65) Prior Publication Data
US 2014/0179959 A1 Jun. 26, 2014

Related U.S. Application Data

(60) Provisional application No. 61/659,124, filed on Jun. 13, 2012, provisional application No. 61/515,048, filed on Aug. 4, 2011.

(51) Int. Cl.
*C01B 3/36* (2006.01)
*C07C 29/48* (2006.01)
(Continued)

(52) U.S. Cl.
CPC ............... *C07C 29/48* (2013.01); *C01B 3/34* (2013.01); *C01B 3/342* (2013.01); *C10G 2/32* (2013.01);
(Continued)

(58) Field of Classification Search
CPC ............ C01B 3/384; C01B 2203/0233; C01B 2203/061; C01B 2203/1241
See application file for complete search history.

(56) References Cited

U.S. PATENT DOCUMENTS 3,966,633 A   6/1976 Friedman
4,211,540 A   7/1980 Netzer
(Continued)

FOREIGN PATENT DOCUMENTS

AU   3893285 A   8/1985
CN   1984840 A   6/2007
(Continued)

OTHER PUBLICATIONS

CN State Intellectual Property Office Search Report; 1st Search; Application No. 2012800413376; Date of Search Completion: Apr. 13, 2015; Examination Department: Electrical Department of Guangdong Center.
(Continued)

*Primary Examiner* — Imran Akram
(74) *Attorney, Agent, or Firm* — Bodi Law LLC; Robert F. Bodi (57) ABSTRACT

A Plasma Arc Reformer for creating a useful fuel, such as Methanol, using any of Methane, Municipal Solid Waste, farm or forest waste, coal orchar rock from oil shale production, petrochemical hydrocarbons, (any carbon containing charge), water, and/or Municipal Sewage, as the source material. A High temperature Plasma Arc de-polymerizes the source material into atoms which, upon partial cooling, creates a gas stream rich in CO and $H_2$ (syngas). Subsequent molecular filter and catalyst stages in the system remove contaminants and produce the output fuel. The system is closed loop with regard to the syngas production in that it recycles the residual unconverted gas and even the exhaust gases if desired. The large amount of heat produced is captured and converted to electric power using a supercritical $CO_2$ Rankin cycle resulting in potentially high efficiencies.

19 Claims, 4 Drawing Sheets (51) Int. Cl.
*H05B 7/18* (2006.01)
*C01B 3/34* (2006.01)
*C10J 3/18* (2006.01)
*C10G 2/00* (2006.01)

(52) U.S. Cl.
CPC ............... *C10J 3/18* (2013.01); *H05B 7/18* (2013.01); *C01B 2203/0216* (2013.01); *C01B 2203/04* (2013.01); *C01B 2203/061* (2013.01); *C01B 2203/0805* (2013.01); *C01B 2203/0861* (2013.01); *C01B 2203/1235* (2013.01); *C01B 2203/1241* (2013.01); *C01B 2203/148* (2013.01); *C10J 2300/1238* (2013.01); *Y02P 20/129* (2015.11); *Y02P 20/544* (2015.11)

(56) References Cited

U.S. PATENT DOCUMENTS

| | | |
|---|---|---|
| 4,339,546 A | 7/1982 | Randalls |
| 4,426,810 A | 1/1984 | Rudolph et al. |
| 4,631,915 A | 12/1986 | Frewer et al. |
| 4,669,270 A | 6/1987 | Frewer et al. |
| 4,861,446 A | 8/1989 | Blom et al. |
| 5,030,661 A | 7/1991 | Lywood |
| 5,437,150 A | 8/1995 | Latham et al. |
| 5,666,800 A | 9/1997 | Sorensen et al. |
| 5,669,216 A | 9/1997 | Ankersmit et al. |
| 5,865,023 A | 2/1999 | Sorensen et al. |
| 5,896,738 A | 4/1999 | Yang et al. |
| 5,974,002 A | 10/1999 | Tsubata |
| 6,214,314 B1 | 4/2001 | Abbott |
| 6,223,519 B1 | 5/2001 | Basu et al. |
| 6,233,914 B1 | 5/2001 | Fisher |
| 6,256,994 B1 | 7/2001 | Dillon, IV |
| 6,260,348 B1 | 7/2001 | Sugishita et al. |
| 6,263,659 B1 | 7/2001 | Dillon, IV et al. |
| 6,290,877 B2 | 9/2001 | Naka et al. |
| 6,298,651 B1 | 10/2001 | Iijima |
| 6,430,916 B2 | 8/2002 | Sugishita et al. |
| 6,463,741 B1 | 10/2002 | Frutschi |
| 6,467,273 B1 | 10/2002 | Lott et al. |
| 6,536,205 B2 | 3/2003 | Sugishita et al. |
| 6,919,062 B1 * | 7/2005 | Vasileiadis ......... C07C 29/1518 423/437.1 |
| 6,968,700 B2 | 11/2005 | Lott et al. |
| 6,976,362 B2 | 12/2005 | Sheppard et al. |
| 7,101,531 B2 | 9/2006 | Kamijo |
| 7,435,760 B2 | 10/2008 | Herling et al. |
| 7,439,274 B2 | 10/2008 | Steynberg et al. |
| 7,485,767 B2 | 2/2009 | Lattner et al. |
| 7,550,635 B2 | 6/2009 | Tio |
| 7,575,730 B2 | 8/2009 | Steynberg |
| 7,612,118 B2 | 11/2009 | Steynberg |
| 7,670,586 B2 | 3/2010 | Wang et al. |
| 7,772,291 B2 | 8/2010 | Steynberg |
| 7,789,048 B2 | 9/2010 | Coffey, Jr. et al. |
| 7,827,804 B2 | 11/2010 | De Koeijer et al. |
| 7,866,160 B2 | 1/2011 | De Ruyck et al. |
| 7,897,649 B2 | 3/2011 | Norbeck et al. |
| 8,008,359 B2 | 8/2011 | Steynberg et al. |
| 8,038,743 B1 | 10/2011 | Wootton et al. |
| 8,105,403 B2 | 1/2012 | Regnery et al. |
| 8,106,102 B2 | 1/2012 | Steynberg et al. |
| 8,123,827 B2 | 2/2012 | Robinson |
| 8,128,898 B2 | 3/2012 | Van Dyk et al. |
| 8,247,462 B2 | 8/2012 | Boshoff et al. |
| 8,268,026 B2 | 9/2012 | Norbeck et al. |
| 8,297,462 B1 | 10/2012 | Joyce |
| 8,320,023 B2 | 11/2012 | Takahashi et al. |
| 8,349,288 B2 | 1/2013 | Norbeck et al. |
| 8,383,078 B2 | 2/2013 | Wang et al. |
| 8,409,008 B2 | 4/2013 | Asami |
| 8,425,636 B2 | 4/2013 | Bommareddy et al. |
| 8,475,549 B2 | 7/2013 | Vogel et al. |
| 8,552,973 B2 | 10/2013 | Ono |
| 2003/0129110 A1 | 7/2003 | Steynberg |
| 2003/0171442 A1 | 9/2003 | Rytter |
| 2004/0045272 A1 | 3/2004 | Miyoshi et al. |
| 2004/0245086 A1 | 12/2004 | Steynberg et al. |
| 2004/0265651 A1 | 12/2004 | Steinberg |
| 2005/0256212 A1 * | 11/2005 | Norbeck ............... C01B 3/34 518/702 |
| 2007/0237691 A1 | 10/2007 | Talata et al. |
| 2007/0256359 A1 * | 11/2007 | Wiltowski ............ C01B 3/16 48/61 |
| 2008/0027150 A1 | 1/2008 | Steynberg |
| 2008/0299022 A1 | 12/2008 | Steynberg et al. |
| 2009/0230024 A1 | 9/2009 | Steynberg et al. |
| 2009/0232729 A1 * | 9/2009 | Genkin ............... C01B 3/384 423/651 |
| 2010/0003556 A1 * | 1/2010 | Hartvigsen ......... B01J 19/088 429/423 |
| 2010/0018116 A1 * | 1/2010 | Mahjoob ............. C01B 3/50 48/77 |
| 2010/0137459 A1 * | 6/2010 | Stites ................. C01B 3/38 518/704 |
| 2010/0156112 A1 | 6/2010 | Held et al. |
| 2010/0158793 A1 * | 6/2010 | Bouillon ........... B01D 53/1475 423/650 |
| 2011/0152593 A1 * | 6/2011 | Kelly .................. C10G 3/49 585/319 |
| 2012/0025140 A1 * | 2/2012 | Tetzlaff ............. B01J 8/067 252/373 |

FOREIGN PATENT DOCUMENTS

| | | |
|---|---|---|
| EP | 0 989 094 A2 | 9/2000 |
| EP | 1375628 A2 | 1/2004 |
| EP | 2124282 A1 | 11/2009 |
| JP | S59167527 | 9/1984 |
| JP | H11188262 A | 7/1999 |
| JP | 2002226870 A | 8/2002 |
| JP | 2003027064 A | 1/2003 |
| JP | 2010077260 A | 4/2010 |
| JP | 2010240621 A | 10/2010 |
| JP | 2010280849 A | 12/2010 |
| KR | 20070033026 A | 3/2007 |
| KR | 20070049614 A | 5/2007 |
| KR | 20090045574 A | 5/2009 |
| KR | 20090068427 A | 6/2009 |
| KR | 10-0953859 B1 | 4/2010 |
| KR | 20100127066 A | 12/2010 |
| KR | 101107384 B1 | 1/2012 |
| WO | 2004112447 A2 | 12/2004 |
| WO | 2008130260 A1 | 10/2008 |
| WO | WO 2008/130260 A1 * | 10/2008 ............... C01J 3/18 |

OTHER PUBLICATIONS

PCT International Search Report; Date of Mailing: Jan. 17, 2013; International Application No. PCT/US2012/049508; International Filing Date: Aug. 3, 2012.
Supplementary European Search Report; Application No. EP 12 81 9786; Place of Search: Munich; Date of Completion of Search: Mar. 4, 2015.
SIPA Supplementary Search Report; Application No. 2012800413376; Date of Search Completion: Sep. 9, 2015; Examination Department: Electrical Department of Guangdong Center.

* cited by examiner

PLASMA ARC FURNACE WITH SUPERCRITICAL $CO_2$ HEAT RECOVERY

CROSS-REFERENCES TO RELATED APPLICATIONS

This application is the national phase of International Application No. PCT/US2012/49508 filed on Aug. 3, 2012, which claims the benefit of priority to U.S. Provisional Patent application No. 61/515,048 filed on Aug. 4, 2011 and U.S. Provisional Patent application No. 61/659,124 filed on Jun. 13, 2012. The entire disclosures thereof are incorporated herein by reference.

BACKGROUND

The invention falls in the area of plasma arc furnaces for the creation of Synthetic gases. Also, this invention uses the chemical process of converting one or more of the Synthetic gases into Methanol with the use of catalysts. Also, this invention falls in the area of electricity generation from waste heat. Also, this invention deals with the disposal of municipal waste in the form of sewage and/or any carbon containing material including pre or post and fill material.

The use of Plasma Arc Furnaces in the creation of syngas (CO and $H_2$) is a technology which is typically located in large installations that occupy acres of and with capital costs in the multi tens to hundreds of millions of dollars. These costs and physical sizes are defined by the system components chosen. These, in turn, are based on electrical energy costs, method of waste heat recovery, process for gas clean up, and value of the end product. The typical plasma arc furnace employs air as a process gas which is electrically heated in a plasma arc torch for raising the material in the furnace vessel to de-polymerization temperatures of around 750-1400 degrees C. The use of air introduces Nitrogen into the high temperature environment of the furnace producing Nitrous and metal oxides in the waste stream. If there is discharge, these pollute the local environmental air.

The problem of processing municipal sewage is a daunting burden for municipalities. Current practice is to biologically neutralize the waste in various stages. This normally includes a bioreactor in which bacteria is utilized to consume and convert most simple nutrients as well as to kill pathogens. The residues are separated in various settling tanks. The eventual output from a sewage processing plant is typically in the form of three products. The first is a theoretically drinkable nearly pure water, the second is a concentrated sludge, and the third is nitro humus fertilizer sent off for packaging and sale to nurseries and gardening.

Improvements to the current state of the art of Plasma Arc Furnace systems would be useful, in particular where one or more of the above identified problems are mitigated.

SUMMARY

Presented is a plasma arc reformer system which produces output fuel, such as Methanol as one choice of product, in a clean and efficient manner. The carbon and the water for the Methanol can come from several different sources, each of which will be briefly described below. The first is to use any Hydrocarbon gas, such as Methane gas, for example, as the source of the carbon and distilled water for the oxygen (both supply hydrogen). The heating of methane with this technology has been developed, as has injecting water in support of Steam reformation or a steam reforming reaction but this invention adds efficient ways to recover the large amount of waste heat that is generated in the process. The second is to use Municipal Solid Waste as an additional source of carbon. The third is to use Municipal water or Municipal sewage as the source of water. Each of these require modifications in the system to handle the other materials present (considered contaminants).

The system discussed herein is primarily facilitated by use of Methane as the process gas instead of air. Methane's electrical properties are very close to air and it can be used in the plasma arc torch. The combination of Methane ($CH_4$), and water ($H_2O$), allows a highly controlled stoichiometric mix of $2H_2+CO$ to be produced. By the use of methane instead of air, little or no nitrogen is available to the furnace environment to lead to nitrogen-based pollutants.

Utilizing the supercritical $CO_2$ ($SCO_2$) hybrid waste heat recovery technology (e.g., see U.S. provisional application 61/636,236), a high percentage of the waste heat is recovered as electricity to run the system. This improves efficiency and lowers the cost by reducing the electrical power expense. This improvement is accomplished by employing heat exchangers in various places in the system, such as, for example, on the furnace vessel surface, the high temperature conduits, the particle precipitators, and the process gas temperature reduction unit prior to gas introduction to the carbonyl molecular filter and then the next one before the reforming catalyst reactor.

Thus, provided is a method of converting a source fuel into an output fuel using a reformer, said method comprising the steps of:
inputting a source fuel into the reformer;
inputting water into the reformer;
providing one or more heat sources in the reformer for breaking down said source fuel and said water into one or more constituent components and/or combinations thereof;
converting at least a portion of said one or more constituent components of the water and the source fuel and/or the combinations thereof into said output fuel using one or more catalysts; and
outputting said output fuel from the reformer.

Also provided is a method of converting a carbon-based input fuel into a desired output fuel using a reformer, said method comprising the steps of:
inputting the carbon-based input fuel into the reformer;
providing one or more heat sources in the reformer for breaking down said input fuel into one or more constituent components and/or combinations thereof;
compressing said one or more constituent components and/or combinations thereof for inputting to a catalyst subsystem;
converting at least a portion of said one or more constituent components of the water and the source fuel and/or the combinations thereof into said output fuel using one or more catalysts;
removing contaminants from said output fuel;
recirculating at least a subset of said contaminants removed from said output fuel back into said catalyst subsystem; and
outputting said output fuel from the reformer Further provided is a reformer for converting a source fuel into an output fuel, comprising: an input for receiving the source fuel; an input for receiving water; a heat source for breaking down said source fuel and said water into one or more constituent components and/or combinations thereof for placing into a flow; a heat exchanger for extracting waste heat from said flow; an engine for converting said waste heat into useful energy; a compressor for compressing said flow received from said heat exchanger; one or more catalyst tanks including at least one catalyst for receiving the compressed flow from said compressor for converting at least a portion of said one or more constituent components and/or combinations thereof into said output fuel; and an output interface for outputting said output fuel.

Also provided is a reformer for converting a source fuel into an output fuel, comprising: an input for receiving the source fuel; a heat source for breaking down said source fuel into one or more constituent components and/or combinations thereof for placing into a flow; a heat exchanger for extracting waste heat from said flow; an engine for converting said waste heat into useful energy; a filter bed for removing catalyst poisoning contaminants from said flow; one or more catalyst tanks including at least one catalyst for receiving the compressed flow from said compressor for converting at least a portion of said one or more constituent components and/or combinations thereof into an output fuel flow; a contaminant removal subsystem for removing contaminants from said output fuel flow for recirculating at least a portion of said contaminants back to said catalyst tanks; and an output interface for outputting said output fuel Also provided are additional example embodiments, some, but not all of which, are described hereinbelow in more detail.

BRIEF DESCRIPTION OF THE DRAWINGS

For a fuller understanding of the nature of the present invention, reference should be made to the following detailed description taken in conjunction with the accompanying drawings.

DETAILED DESCRIPTION OF THE EXAMPLE EMBODIMENTS

Provided is a plasma arc reformer system for creating a useful fuel, such as Methanol, using any of Methane, Municipal Solid Waste, farm or forest waste, coal or char rock from oil shale production, petrochemical hydrocarbons, (any carbon containing charge), water, and/or Municipal Sewage, as the source material. A High temperature Plasma Arc de-polymerizes the source material into atoms which, upon partial cooling, creates a gas stream rich in CO and $H_2$ (syngas). Subsequent molecular filter and catalyst stages in the system remove contaminants and produce the output fuel. The system is closed loop with regard to the syngas production in that it recycles the residual unconverted gas and even the exhaust gases if desired. The large amount of heat produced is captured and converted to electric power using a supercritical $CO_2$ Rankin cycle resulting in potentially high efficiencies.

The reformer system is capable of producing Methanol which, along with being utilized as a portable fuel, reduces or eliminates pollution to atmospheric air and also includes improvements to the waste heat recovery system. These improvements reduce system size and cost. Also presented is an architecture and process for the de-polymerization of Sewage and/or Municipal Solid Waste to create syngas and ultimately upgraded Catalyzed hydrocarbons an example of which is Methane or Methanol.

Components useful in accomplishing these features are discussed in U.S. provisional application 61/636,236 (Improved Performance of a Transcritical or Supercritical $CO_2$ Rankin Cycle Engine) that was filed on Mar. 20, 2012, and is incorporated herein by reference, which discloses an engine useful for heat recovery, and the material in U.S. patent application Ser. No. 13/074,510 (Oscillating Piston Engine) that was filed on Mar. 29, 2011, also incorporated by reference, and U.S. provisional application 61/625,940 filed on Apr. 18, 2012, disclosing an polygonal oscillating engine, also incorporated by reference, that discuss additional engine designs that can be useful for heat recovery purposes as provided herein.

First Example Configuration

Figure 1:
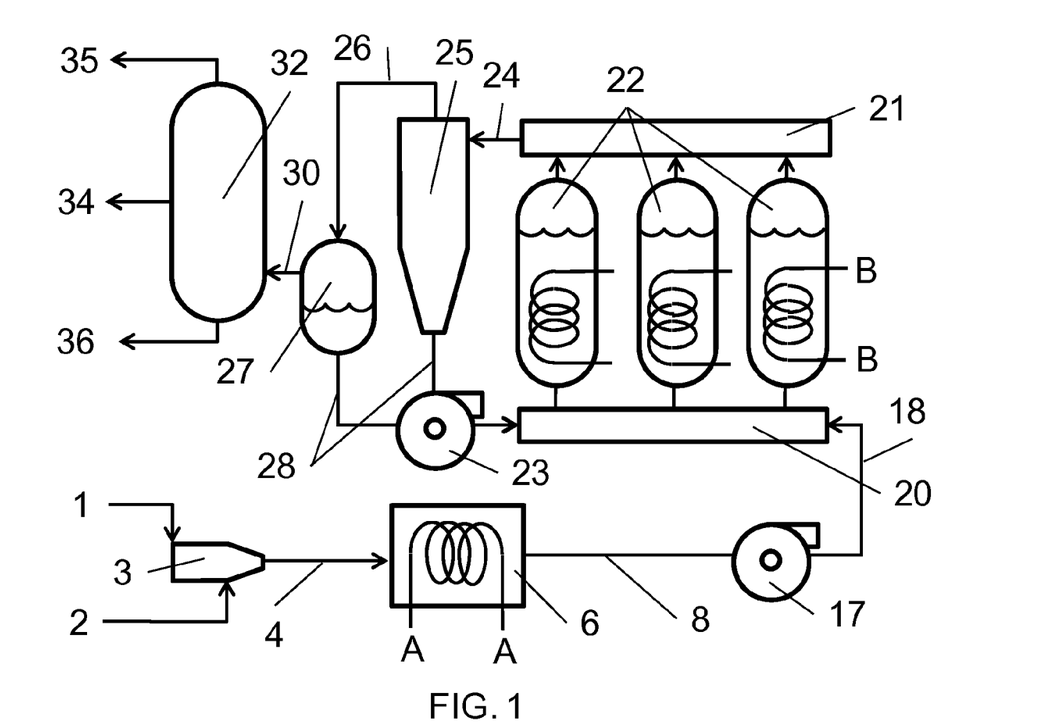
FIG. 1 shows a block diagram of the basic system creating Methanol from a Methane/water mix, with the primary locations for recovering waste heat.

FIG. 1 shows the primary elements in the basic system for creating Methanol from Methane and water. The main working element is a plasma torch 3 in which the operating gas Methane is introduced at input 1 under high pressure and into which water 2 is mixed downstream. The output 4 contains a mixture of atoms of carbon, hydrogen, and oxygen at very high temperature (>750 degrees C.). This combination is cooled in a heat exchanger 6 where the cooling fluid such as Polyol Ester oil for a non-pressurized heat transport system or even water under pressure A circulates to a heat recovery system described below. The fluid at output 8 is now a mixture of carbon monoxide (CO) and hydrogen gas ($H_2$) (synthetic gas, or syngas) with a small amount of carbon dioxide ($CO_2$). This material compressed by compressor 17 prior to providing to the manifold 20. The gases at manifold input 18 are at approximately 200-250 degrees C. required by the up-coming catalytic converters 22. This temperature is established by controlling the flow rate of the cooling fluid A in the heat exchanger 6. At this point the designer may choose to include a high volume compressor or compressors, prior to the catalysts. In this architecture the syngas product temperature is reduced to the lowest discharge temperature of the waste heat recovery system, being approximately 35 C. Then by use of the mentioned compressor, the temperature is raised to the input temperature of the catalysts. This would be after the temperature dropping heat exchanger, to allow the furnace section to operate at or below ambient pressure prior to the catalysts, which gain efficiency at higher pressures. This can provide a significant improvement to system operation as the freedom to have the hot section operating at pressures permitting simple and inexpensive seals made from vermiculite as one example are less difficult to provide into the syn gas processing gas circuit.

The design includes the manifold 20 that splits the flow and directs it to series-bypass circuit elements (the catalyst array runs in a series circuit, the tank to be switched out for maintenance is plumbed to a manifold, that allows parallel switching or bypassing, so as to isolate that or any individual tank) for separate catalyst columns 22. Each catalyst container can be individually removed from the manifold gas circuit for maintenance (such as catalyst exchange) while the overall system continues to produce product. The reaction in the catalyst tank is exothermic and operates only in a narrow temperature range. Therefore each tank has its own thermal exchange system, with the cooling fluid (Polyolester or Mineral oil as an example or pressurized water) B circulating to a second heat recovery system. This heat recovery system is separate from the system using fluid A because of the fairly large differences in temperature, allowing for local optimization of the heat recovery systems. The catalyst column 22 is described in more detail below.

A collection manifold (such as a single pipe feeding syngas into the compressor) 21 gathers the output from each of the catalyst columns via a single output pipe. This exit manifold now contains gaseous or vaporized methanol, some unconverted syngas, and droplets of the oil slurry containing the catalyst particles. This output is directed 24 to a cyclone separator 25. The cyclone separates most of the particles from the gases. The particles (oil droplets and catalyst particles) pass out of the bottom 28 and return to the input manifold 20. The gases pass through 26 to a condenser 27. This condenser separates any remaining oil vapor from the methanol and syngas and lowers the temperature to approximately 70 degrees C. (methanol is still a gas), after which the output 28 is condensed by compressor 23. The condensed oil returns to the catalyst slurry in the catalyst columns 22 via the compressor 23 to the input manifold 20 for reuse/reprocessing.

The output of the condenser 27 is primarily methanol (~96%), but it does contain some syngas and some higher weight compounds of carbon, hydrogen, and oxygen. This mixture is sent via output 30 to a methane refinery column 32 which separates out the final methanol product in output 34 from the other gases usually via condensation at or below 67 degrees centigrade. The syngas via output 35 is returned to the system through the input manifold 20 for reuse/processing. The designer has the choice at this point, in the gas circuit, to direct all non-condensed gas products to a generator system. The higher weight compounds are provided via output 36 and are returned to the system through the water inlet 2 to be decomposed and run through the system again.

Second Example Configuration

Figure 2:
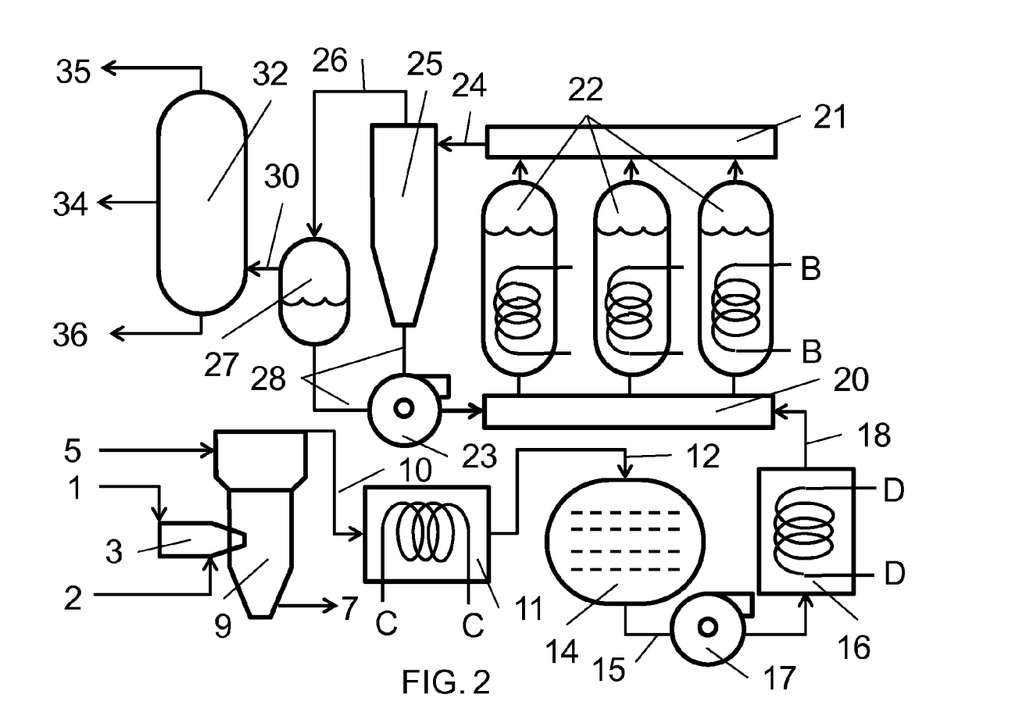
FIG. 2 shows the modifications to the basic system when Municipal Solid Waste is used as a source of additional carbon or Municipal Sewage is used as the source of water.

FIG. 2 shows some desired changes to the basic system described above when it is being used for disposal of Municipal Solid Waste or Municipal Sewage. In this example variation, the changes are primarily provided in the front end prior to the manifold 20 leading to the catalyst columns. For the case of handling the Municipal Solid Waste, the feed stock (chopped up solid waste) is fed via input 5 into a more classic plasma arc furnace 9. This source of carbon changes the flow ratio of methane at input 1 and water at inlet 2 so that a stoichiometric mix is still produced at the output of the furnace 10. The slag elements from the Municipal Waste are collected at the bottom of the furnace and extracted via output 7.

For the alternative case of handling Municipal Sewage, the feed stock is now liquid with the major component being water. This requires a different desired amount of methane to be provided from input 1 and different amount of water from inlet 2 (if any since all the water may be in the sewage) and a different mix of elements in the slag output 7. But the feed gas (water and Methane) ratios are set to produce a stoichiometric mix as close as possible in the output of the furnace 10. For sewage the ratio is $CH_4+H_2O=CO+3H_2$, with the carbon from organic materials being a very very small fraction, but the carbon would be accounted for by adjusting the $CH_4$ lower. For Municipal solid waste, Forest or Farm waste, there is an approximation of the input charge by using Cellulose as the feedstock example, which is $C_6H_{10}O_5$. This can also be thought of as $(6C+5H_2O) +8CH_4+9H_2O=14CO+58H+14O$. The oxygen and hydrogen atoms will then tend to combine to form $7O_2$ and $29H_2$. Since the balanced syngas input ratio for Methanol (being $CH_3OH$) would be $CO+4H$ or $CO+2H_2$ then we would have the precursors for 13 $CH_3OH+6H$. The extra Hydrogen would be the principal fuel for the subsequent generator option.

The vapor output 10 from the arc furnace 9 in FIG. 2 will typically be different from the vapor output 4 from the plasma torch of the embodiment of FIG. 1 due to the material that is in the feed stock in the furnace. In the case of these waste processing examples, some of these elements could poison the catalyst in the columns 22 so it is desired to include a catalyst filter bed acting as a molecular filter 14 with the purpose of removing from the stream any elements that could poison the catalyst in 22. The temperature provided in this new filter bed 14 should be lower than the separator output 10 to accommodate the metals used in the containment vessel of the molecular filter, this is typically in 500 C range but higher than the temperature in the manifold 20. Therefore, there are provided two heat exchangers 11 and 16 added in FIG. 2 which are different from the heat exchanger 6 in FIG. 1 in that the cooling fluids C and D are at different temperatures from the cooling fluid A. Examples of acceptable cooling fluids include Polyol Ester Oil, which has the highest operating temperature for oil, Mineral Oil is good up to 350 C, and one could even use liquid metals such as mercury, Water under pressure would work as well Furthermore, compressor 17 now inputs the flow from the filter 14 output 15, and outputs the compressed stream into the heat exchanger 16. The gases input in line 12 are the same as the gases in output 10 only at a lower temperature and may contain catalyst poisons such as Sulfur, Arsenic, and/or Chorine. The gases at output 15 of the filter bed 14 are mainly components of syngas (CO and $H_2$) since any poisons have been removed by the catalyst filter bed 14.

The input to the catalyst manifold 20 via input 18 in FIG. 2 is typically provided at the same temperature as via input 18 in FIG. 1. Hence, the remaining part of the system operates the same as described above regarding FIG. 1.

Heat Recovery System

Figure 3:
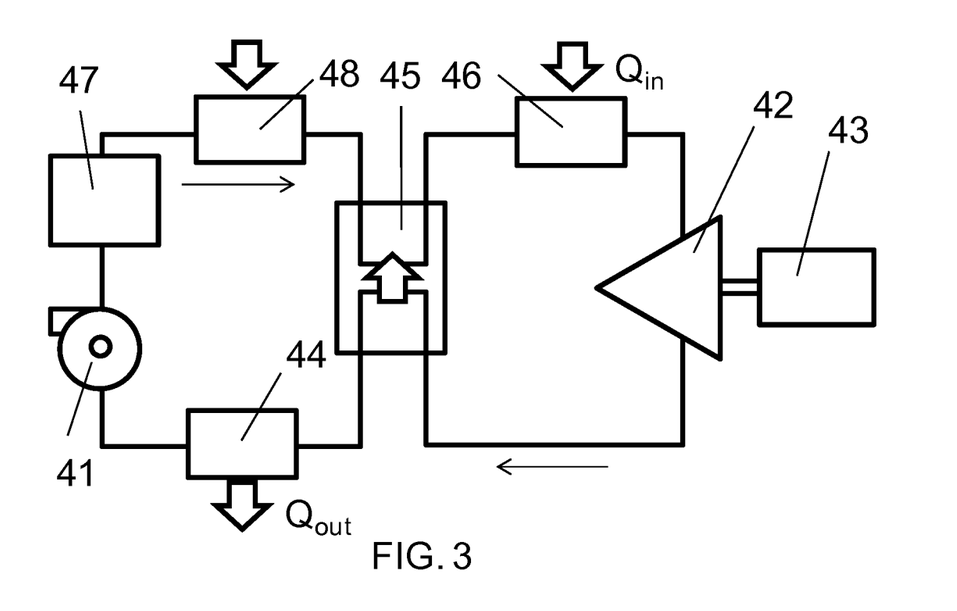
FIG. 3 shows the block diagram of the supercritical $CO_2$ waste heat recovery system that is used in several places in systems mentioned above.

FIG. 3 shows the elements of a heat recovery system that can be used with the example furnaces. An example of such a system is described in U.S. provisional application 61/636,236 (improved Performance of a Transcritical or Supercritical $CO_2$ Rankin Cycle Engine) that was filed on Mar. 20, 2012 and is incorporated herein by reference. The system has a compressor 41 that compresses supercritical $CO_2$ from a pressure above the critical pressure (>74 bar) to a pressure ~200 bar (or less). The $CO_2$ flows through a pressure/flow control device 47 that regulates the flow rate, then through an optional heat exchanger 48 used for low temperature heat (that could come from the condenser 27 in FIG. 1, for example). A key element of the heat recovery system is the internal heat exchanger 45 which moves heat from the high temperature low pressure side to the lower temperature high pressure side. Then the supercritical $CO_2$ enters the primary heater 46, and this hearer is fed by the heat flow A or B in FIG. 1, or in heat flow B, C, or D in FIG. 2. This raises the temperature of the supercritical $CO_2$ to ~450 degrees C. for the case of flow from A or C, and to ~250 degrees C. for the case of flow from B or D.

A heat exchanger 46 is used to heat $CO_2$. The heated $CO_2$ then enters the expander 42 which drives a permanent magnet alternator 43 and converts the thermal energy into electrical energy. This electrical energy is used to supplement the power required by the plasma arc torch array and thereby increase the overall efficiency of the methanol production. The lower pressure $CO_2$ then completes the cycle by passing through the internal heat exchanger 45 and a coder 44 before arriving back at the compressor 41.

Figure 4:
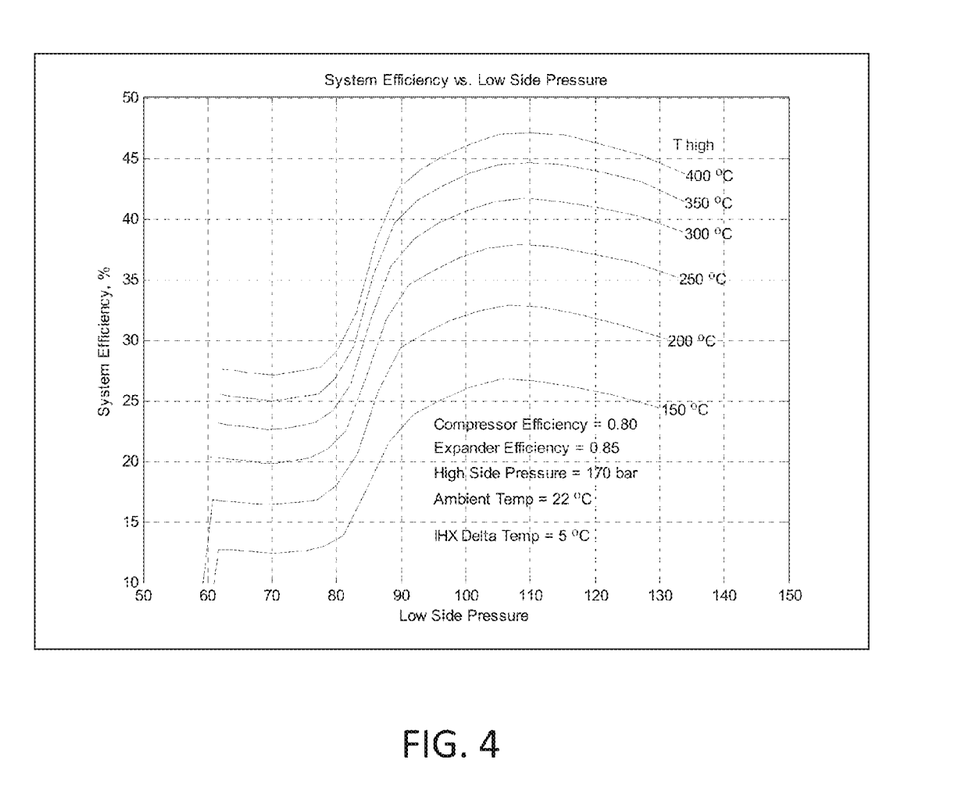
FIG. 4 is a series of plots showing example system efficiencies.

The efficiency of the heat recovery system depends on the specific choices of pressure and temperature. For the lower temperature heat exchangers, the efficiency can be ~25% and for the higher temperature heat exchangers, the efficiency can exceed 40%. The validated example uses compressor and expander efficiencies of 80% and 85% respectively. Due to the option of operation of these two components in the example system using oil as both lubricant and seal, the efficiency could be about 92% each. FIG. 4 shows plots of examples of such efficiencies versus system low-side pressures.

The Plasm Arc Furnace

In a basic example system, the plasma arc furnace is primarily made up of plasma arc torches in an array (there is no slag). Electric arc torch heating or Induction coupled plasma torch heating could be utilized. All the plasma arc torches are fed by high pressure Methane gas ($CH_4$) resulting in a flame approximately 5500 degrees C. composed of carbon and hydrogen ions. Downstream from the plasma generator section, water ($H_2O$) is injected which immediately decomposes into oxygen and hydrogen ions. The gas and water flow is set to give a near stoichiometric mix of one carbon on for one oxygen ion and four or more hydrogen ions at a temperature of approximately 750-1400 degrees C. Much of the heat reduction comes from expansion of the gases, but the walls of the chamber are also cooled, with the cooling liquid being used to drive the waste heat recovery system described below. The resulting gas mix is primarily CO and $H_2$ with a small amount of $CO_2$.

For the example application of using Municipal Solid Waste as an additional source of carbon, the furnace architecture is an insulated vertical cylinder lined with refractory bricks, with a closed top and bottom end, and with an array of torches around its lower section. Methane and water are heated by the plasma torch as they enter the furnace vessel. There, the carbon containing charge is heated to very high temperature where it decomposes into its constituent atoms. The volumetric mix of Methane, water and Municipal Solid Waste is set to produce the stoichiometric $H_2$ and CO gas mix. This process also has other atomic species present from the Waste. Some of these appear as slag accumulating at the bottom of the furnace. Others remain gaseous, and are separated at a later stage in the system.

For the case of using Municipal Sewage, one deviation from conventional practice involving plasma arc furnaces is the fact that there is no real need for a large furnace vessel. Instead, the system(s) disclosed herein can be made much smaller than conventional systems, such that there may be an array of torch nozzles rather than the more conventional large vertical cylinder. The main difference from other examples provided above is in the ratio of materials used to keep the stoichiometric mix of the syngas and in the amount of slag products collected.

In each case, the preferred embodiment is for the furnace casing to be made of high temperature steel or Nickel containing alloy such as Stainless Steels or Inconel, lined with a layer of refractory bricks on the inside, and with cooling tubes bonded to the outer wall of the furnace vessel. This would be followed with a second case that was held away from the inner case with standoff ribs between the inner and outer case to act as an insulating or heat retaining muffle. The cooling tubes, bonded to the inner case, function to capture the waste heat from the furnace and convey it, via pumped flowing oil, to the heat recovery system.

The Heat Recovery System

The heated Syngas can be recycled through a heat exchanger used as part of the Supercritical $CO_2$ Expander Rankin Cycle Engine (see application Ser. No. 13/074,510, incorporated herein by reference), to capture and covert waste heat into electricity to supplement the main power supply. Each step in the heat reduction is a potential location for the Supercritical Carbon Dioxide Rankin Cycle Engine waste heat recovery system. In this manner, a high fraction of the waste heat is converted to electric power to run the system and improve its efficiency. Alternatively, a recovery engine can be modeled after a polygonal engine as disclosed in U.S. provisional application Ser. No. 61/625,940, incorporated herein by reference.

The effect of the heat recovery system is to improve overall system efficiency and also reduce the reformer plant's size relative to a conventional refinery or plasma arc furnace system.

The Methanol Creating Catalyst

The preferred example embodiment of the catalyst has been developed elsewhere and demonstrated in 2004 by Air Products and Chemicals, Inc. in partnership with Eastman Chemical Company where they successfully demonstrated a Liquid-Phase Methanol production process. Such catalysts can include Copper Oxide Zinc Oxide and/or Nickel, or even Cobalt and/or Manganese. The stoichiometric balanced gas stream is usually pumped under pressure into a reactor vessel where it mixes with catalyst slurry and is converted into methanol vapor. The catalyst slurry is usually comprised of copper and zinc oxides suspended in mineral oil.

The reaction is exothermic and typically will be maintained between 215 and 270 degrees C. In this situation the syngas conversion to methanol releases heat and, if not cooled, would drive the catalyst temperature up until the conversion process would stop. The heat is removed by heat exchange tubes in the reactor and is another source of heat for the waste heat recovery system. The temperature is controlled by the rate of the cooling fluid (oil) flowing in the reactors. The conversion process produces greater than 96% Methanol.

Exiting the reactor is a mix of methanol, unconverted syngas, excess Hydrogen, and some of the slurry containing the catalyst. This is subsequently separated in a cyclone separator, with the slurry being returned to the catalyst reactor and the gases proceeding to further processing.

After the converted and unconverted syngas leaves the cyclone separator, it is a gas which is at an elevated temperature. The temperature is lowered in a condenser, but stays above the condensation temperature of the Methanol. In the case of Methanol, the temperature is about 65 degrees C. In this manner the heavier reactant products are separated and returned to the plasma arc furnace or directed to an electric power generator.

The Guard Bed Filter

A non-trivial amount of effort is provided for removing the catalyst poisons in the gas stream from the Municipal Solid Waste or the Municipal Sewage. Scrubbers exist to deal with this issue, so off-the-shelf technology could be utilized. These scrubbers can operate at temperatures intermediate between the output of the plasma arc furnace and the input to the methanol producing catalysts, with the operating temperatures usually being determined by the materials used to make the containment vessel, typically a 480° C. rated or higher steel is used with the typical input temperature of the syngas being 500° C.

Heat exchangers are used to lower the gas temperature from the furnace to the acceptable temperature of the guard bed molecular filter (which typically is ~500 degrees C.).

The guard bed filter is similar to a catalyst, but, rather than creating a desired compound, its purpose is to react with, trap, and remove a contaminant that could later in the system neutralize the Methanol catalyst material. An example composition of this filter would be Manganese Oxide dispersed on an activated charcoal matrix, though there are other alternatives. This filter would absorb the Arsenic, Sulfur, and/or Chlorine trace quantities that might be in the feedstock.

After the guard bed filter, there will typically be provided another heat exchanger to lower the syngas to the acceptance temperature of the compressor then catalyst converter. This acceptance temperature is catalyst dependent but for the smaller liquid phase catalyst reactors designed to produce methanol the input temperature would be 235±15 degrees C.

Other Elements

There is a particle cyclone separator which is used to remove the particles and some oil droplets that are carried out of the methanol catalyst columns. This separator could also have heat transfer tubes built into the walls so as to make it a heat exchanger as well. The cyclone separator will catch most of the oil droplets, but some oil vapor will pass through. This cyclone separator works by having a gas with particles introduced at the bottom side and being withdrawn at the top. The gas moves in a tornado-like vortex in moving from bottom to top. The particles being heavier are flung out to the wall. Friction by contact with the wall lowers the momentum of the particle and gravity draws it to the bottom where a collector trap is located. The gas exit is at the center top. In an example embodiment, welded tubes are provided on the outside and a separate baffle layer is provided to first remove the heat in a metal cone of the case and second to trap heat in the air space between the inner and outer wall.

Following the cyclone, then, is a condenser that reduces the temperature to just above the methanol liquid temperature (dependent upon the exact pressure in the system at this stage). This condenser will remove all heavy molecules and the remaining oil vapor.

The final stage is a methanol refinery. This stage is to clean up the methanol to the purity desired by the customer. This refinery will return any syngas that is still unconverted to the catalyst cycle, or generator input and any heavier non-methanol products to the furnace to be recycled.

Alternate Products and Uses

The choice of catalyst will determine the produced hydrocarbon product. Methanol, Ethanol, Methane, or poly aromatic hydrocarbons such as Olefins can all be produced, as desired, although the examples provided herein focus on the production of methanol. But many of these or other hydrocarbon fuels could be used to run the system's primary power generators. Further, the syngas produced could be fed into the generator engine if so architected. Hence, it is not important what the source is for the primary power to run the plasma arc and the required pumps.

The primary product from the example systems provided herein is Methanol, which is one of the cleanest of liquid fuels. If large generators are run on this fuel, only $CO_2$, $H_2O$ and Nitrogen from air which is neutral to the process are generated as the exhaust gases from the generator. If the desired product is also $CO_2$, this exhaust gas can be cooled and compressed, the water vapor removed and recycled, and the $CO_2$ compressed and condensed to its liquid state. This liquid could be used at tar sand and oil recovery sites, as the Liquid $CO_2$ is an environmentally benign detergent. This application replaces water and steam use at such sites, and thereby increases oil recovery while reducing or eliminating environmental pollution issues. It is also possible to recover the exhaust products, separate them from the nitrogen then to recycle them through the Reformer system.

Potential Applications

Reformation means conversion of all carbon by electric heated hydrocarbon gas plus water and high temperature plasma depolymerization into synthetic gas, comprising primarily a ratio of one carbon monoxide molecule (CO) and 2 or more molecules of Hydrogen gas ($2H_2$). Catalytic conversion is basically the use of a catalyst that will take the syn gas product and link the gas components to any number of products, Methanol can be one, Methane, Ethane, olefins, Dimethyl Ether are just a few.

Power Generation is a byproduct resulting in electricity generation using the fuel gas discharge from left over syn gas and extra hydrogen for fueling an electric power generator, which can be any generator but specifically using one of the engines cited in the application Sewage (as a Water Source) reformation to syn gas then catalytic conversion to Methanol—with waste power output is a useful application.

Municipal Solid Waste (MSW) alone (via a plasma arc furnace using the a gas-to plasma feed) or with sewage reformation to syn gas and then catalytic conversion primarily producing Methanol-and waste power generation is another application.

Farm or Forest waste reformation to syn gas then catalytic conversion with sewage or MSW and waste power generation is another application.

Coal reformation to syn gas then catalytic conversion using sewage and waste power generation is another application.

The processing of Carbonate rock strata from shale oil processing to syn gas then catalytic conversion is another application.

Carbon Dioxide, as a liquid production from above example gas feedstock. CO would be condensed via compression and cryogenic separation from the hydrogen with subsequent combustion to produce $CO_2$ with electric power and compression and cryogenic processing to a liquid.

$CO_2$ from the above processes could be used as a liquid in Shale Oil recovery via shale rock agitation in Liquid $CO_2$. This will result in a higher recovery rate with a lower cost than other processes. $CO_2$ would be injected into depleted oil wells, in low production or old fields, with high pressure Fracking as an option. This method is most productive when the $CO_2$ is liquid in the reservoir, up to this point the oil yield is typically 20% higher than baseline outputs.

On ship (e.g., at an oil platform) applications include: Reformation to syn gas then catalytic conversion of offshore Methane in Natural gas deposits is an application; and Reformation to syn gas then conversion of Natural gas to $CO_2$ via above process(es);

On Platform applications include: Reformation to syn gas then catalytic conversion of Natural gas to Methanol; On Platform oil upgrading via reformation to syn gas then catalytic conversion to other desired products—on or offshore; On Platform $CO_2$ production for Undersea injection as a fracking agent to aid in Oil recovery in undersea shale oil, Tar sand deposits or as a washout agent for increased oil field recovery.

Reformation with unconverted syn gas and Hydrogen used as a reducing process gas in a separate plasma arc furnace for smelting of ores and or reduction to metal billet is another application. This would permit subsequent processing to desired form of alloys and ores. In this version the Reformer is still used as claimed in the description body, however the second use is for the production of, principally hydrogen gas for metal recovery or production as a combined waste to electricity plant with a combined metal production plant as well.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. R is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method of converting a source fuel into an output fuel using a reformer, said method comprising the steps of:
   inputting a source fuel into a furnace of the reformer, wherein said source fuel includes waste material from sewage or solid wastes including carbon;
   inputting methane into the furnace as another source fuel;
   inputting water into the furnace;
   providing one or more heat sources in the reformer for breaking down said source fuels and said water into one or more constituent components and/or combinations thereof;
   converting at least a portion of said one or more constituent components of the water and the source fuels and/or the combinations thereof into said output fuel using one or more catalysts;
   outputting said output fuel from the reformer; and
   recovering waste heat of said reformer to generate electricity using a rankin process using a rankin engine driven by carbon dioxide.

2. The method of claim 1, wherein the step of converting waste heat of said reformer into electricity includes a generator, and wherein said rankin engine is an oscillating disk piston engine adapted for driving said generator.

3. The method of claim 1, wherein said rankin engine is driven by super critical carbon dioxide.

4. The method of claim 1, wherein said output fuel includes methanol.

5. The method of claim 1, wherein said catalyst includes one or more of Copper Oxide, Zinc Oxide, and/or Nickel.

6. The method of claim 1, wherein said heat source is a plasma arc source.

7. The method of claim 1, wherein said method provides for the complete recovery of all $CO_2$ and other exhaust gas products thereby providing for zero emission power generation and recycling of said $CO_2$.

8. The method of claim 7, wherein said method provides for fuel creation via syn gas generation.

9. The method of claim 1, further comprising the step of removing contaminants from said converting step using a cyclone separator.

10. The method of claim 1, wherein said one or more heat sources raise said methane and water inputs to depolymerization temperatures of 750 degrees Celsius or above.

11. A method of converting methane into methanol using a reformer, said method comprising the steps of:
    inputting methane into a furnace of the reformer;
    inputting water into the furnace;
    inputting waste material from sewage or solid wastes into the furnace;
    providing one or more heat sources in the furnace for breaking down said methane, said waste material, and said water into one or more constituent components and/or combinations thereof;
    converting at least a portion of said one or more constituent components of the water and the source fuel and/or the combinations thereof into said methanol using one or more catalysts;
    outputting said methanol from the reformer;
    and recovering waste heat from the reformer using a rankin process utilizing supercritical carbon dioxide as a working fluid.

12. A method of converting a source fuel into a desired output fuel using a reformer, said method comprising the steps of:
    inputting the source fuel into a furnace of the reformer, wherein said source fuel includes waste material from sewage or solid wastes including carbon;
    inputting methane into the furnace as another source fuel;
    inputting water into the furnace;
    providing one or more heat sources in the reformer for breaking down said source fuels and said water into one or more constituent components and/or combinations thereof;
    compressing said one or more constituent components and/or combinations thereof for inputting to a catalyst subsystem;
    converting at least a portion of said one or more constituent components of the water and the source fuels and/or the combinations thereof into said output fuel using one or more catalysts;
    removing contaminants from said output fuel;
    recirculating at least a subset of said contaminants removed from said output fuel back into said catalyst subsystem;
    outputting said output fuel from the reformer; and
    recovering waste heat from the reformer using a rankin process utilizing carbon dioxide as a working fluid to generate torque; and generating electricity using said torque.

13. The method of claim 12, wherein said contaminants include syn gas.

14. The method of claim 12, further comprising the step of removing waste heat from said one or more constituent components and/or combinations thereof for providing to an energy capture device.

15. The method of claim 12, wherein said method provides for the complete recovery of all $CO_2$ and other exhaust gas products thereby providing for zero emission power generation and recycling of said $CO_2$.

16. The method of claim 12, wherein said output fuel includes methanol.

17. The method of claim 12, wherein said source fuel includes sewage waste.

18. The method of claim 12, wherein said source fuel includes cellulose.

19. A method of converting a carbon-based source feel into a desired output fuel using a reformer, said method comprising the steps of:

inputting the carbon-based source fuel into a furnace of the reformer, wherein said carbon-based source feel includes waste material from sewage or solid wastes;

inputting methane into the furnace:

providing one or more heat sources in the furnace for breaking down said source fuel and methane into one or more constituent components and/or combinations thereof;

compressing said one or more constituent components and/or combinations thereof for inputting to a catalyst subsystem;

converting at least a portion of said one or more constituent components of tile water and the source fuel and/or the combinations thereof into said output fuel using one or more catalysts;

removing contaminants from said output fuel;

recirculating at least a subset of said contaminants removed from said output fuel back into said catalyst subsystem;

outputting said output fuel from the reformer; and recovering waste heat from the reformer using a rankin process utilizing supercritical carbon dioxide as a working fluid to generate torque; and generating electricity using said torque.

* * * * *